United States Patent [19]
Worthington

[11] Patent Number: 6,068,481
[45] Date of Patent: May 30, 2000

[54] FLEXIBLE DIMENSION TEMPORARY AND LONG-TERM PROVISIONAL CROWNS

[75] Inventor: Mark L. Worthington, Eugene, Oreg.

[73] Assignee: Flexible Dimensions, LLC, Eugene, Oreg.

[21] Appl. No.: 09/178,023

[22] Filed: Oct. 23, 1998

Related U.S. Application Data

[60] Provisional application No. 60/063,410, Oct. 28, 1997.

[51] Int. Cl.$^7$ ........................................ A61C 5/08
[52] U.S. Cl. .......................................... 433/219; 433/218
[58] Field of Search ........................... 433/40, 218, 219

[56] References Cited

U.S. PATENT DOCUMENTS

| | | | |
|---|---|---|---|
| 4,015,332 | 4/1977 | Manne | 433/219 |
| 4,678,435 | 7/1987 | Long | 433/218 |
| 4,778,386 | 10/1988 | Spiry | 433/45 |
| 4,795,345 | 1/1989 | Ai et al. | 433/202.1 |
| 5,458,489 | 10/1995 | Tennyson | 433/181 |

*Primary Examiner*—John J. Wilson
*Attorney, Agent, or Firm*—Marger Johnson & McCollom, P.C.

[57] ABSTRACT

A set of fiber-polycarbonate shells for making bicuspid and molar crowns is formed with lingual sidewalls shorter than the facial or buccal sidewalls to facilitate easy fit both gingivally and occlusally. The shells are sized to fit loosely between adjacent teeth and relative to opposed teeth. The shells have windows in the mesio-distal sidewalls and can have a window in the occlusal wall. A new method of forming crowns using such shells provides a good fit to a prepared tooth and relative to adjacent and opposed teeth by filling the shell with a glass-filled acrylic resin filler, biting down on the filled shell to position the shell gingivally and occlusally. Resin filler extrudes through the window to form good proximal contacts and to shape the occlusion, with the shell rocking about the facial gingival margin to a comfortable fit with an opposed tooth. The excess resin filler and shell are easily shaped to form the final crown. The crown, formed by polycarbonate reinforced resin, is durable enough for long-term wear.

41 Claims, 6 Drawing Sheets

FLEXIBLE DIMENSION TEMPORARY AND LONG-TERM PROVISIONAL CROWNS

RELATED APPLICATION DATA

This application claims priority from inventor's provisional application Ser. No. 60/063,410, filed Oct. 28, 1997, for Flexible Dimension Temporary Crowns.

BACKGROUND OF THE INVENTION

This invention relates generally to temporary and provisional dental crowns, and more particularly to flexible dimension crown shells and methods of making temporary and provisional dental crowns using such shells. Presently, there are three primary methods for the fabrication of temporary and provisional crowns. In the first technique, conventional prefabricated crown forms or shells, made of a metal such as aluminum or stainless steel, or of polycarbonate such as the Ion crown forms sold by 3M Corporation, are trimmed and shaped to fit a prepared tooth. Other examples of temporary crowns of this type are disclosed in U.S. Pat. Nos. 4,015,332 (Manne); 4,678,435 (Long); 4,778,386 (Spiry) and 5,458,489 (Tennyson).

The second technique calls for making an impression of the tooth before the tooth is prepared for a crown. Then the impression is filled with a bis-acryl material and placed over the prepared tooth. The material sets and is then removed from the dental impression, trimmed, polished and seated in the mouth.

The third primary technique, used and recommended by Gordon Christenson, is also popular. A putty-like ball of polymethyl-methacrylate is applied over a prepared tooth, the patient bites down, and the material begins to set. Before it completely sets, the putty-like material is removed from the tooth, trimmed and placed back on the tooth. The set material is then trimmed and the bite is adjusted, and the temporary crown is cemented to the tooth. A variation in this technique, disclosed in U.S. Pat. No. 5,385,469, uses a tubular dental form for forming a universal crown in situ.

Each of these techniques has various advantages and disadvantages. The first technique, using prefabricated forms, is fast and simple, but the fit of the conventional shell is not very good. The margins do not fit well. It is hard to get good proximal contact to adjacent teeth, and the contours and occlusion are not always good. Some manufacturers try to overcome these drawbacks by proliferating sizes and shapes of the shells. This approach is expensive, and turns out to be very time-consuming for the dentist to pick the right size and shape out of a selection of as many as 80 different sizes and shapes of molars and bicuspids. Manne adds a degree of freedom by providing an incisor shell that has slits in the mesio-distal sides to permit the shell to flex in the labio-lingual direction about a hinge axis at the occlusal surface. Long provides a degree of freedom in a temporary molar crown by having the mesio-distal sides open to permit the acrylic resin filler material to protrude proximally to contact adjacent teeth. These shells, like others used in this technique, require trimming the free edges of the buccal and lingual sidewalls to assure a good fit along the gingival margins as well as a good occlusion. The Long shells, with open mesio-distal sides, also appear to require substantial trimming of the filler material. Such trimming and fitting is time-consuming for the dentist and patient.

The second technique gives good contours and bite accuracy but it is time-consuming and the strength and durability of the temporary crowns are not very good. Making impressions is time-consuming, and cannot be done if the patient's tooth is already broken when initially treated. The third technique of free-forming a temporary of putty-like material is accurate and fairly fast if performed by a skilled dentist or technician. The main problem with this approach is that it is very technique-sensitive. A dental technician must be highly skilled in order to carve accurately the tooth anatomy. Another problem is that special care must be taken to assure that the patient's mouth is not injured by the exothermal reaction that is involved in the curing of the putty-like material.

All of the foregoing techniques take a half an hour or more work for the dentist to fit a temporary or provisional crown to a patient. The resulting temporary or provisional crown is typically not very durable and therefore not well-suited for long-term wear. An exception is stainless steel shells which are very durable but these are more difficult to fit and to grind the occlusal surfaces to get a good comfortable bite.

Accordingly, a need remains for a way to make temporary and provisional crowns that is quick and accurate, provides a good fit without much trimming, is durable enough for long-term use, and is inexpensive.

SUMMARY OF THE INVENTION

It is, therefore, an object of the invention to simplify the fabrication, fitting and installation of temporary and provisional crowns.

Another object of the invention is to make temporary and provisional crowns that fit well and are durable enough for long-term use.

A further object is to make crowns that fit well but are inexpensive both in terms of materials and time taken to fit the crowns.

In general, the invention combines the advantages of two of the conventional techniques that are used today, using both free-form techniques and specially-designed shells, in a way that avoids the major disadvantages of these techniques as used individually. The shells have windows in the in the mesio-distal sidewalls. A putty-like material or resin is used, similar to that used in the free-form technique but shape-controlled by the shell and the partial windows provided therein, which saves the dentist time in shaping the temporary crown. The mesio-distal sidewalls each include a recessed area or indentation adjoining the windows for receiving and retaining protruding resin in proximal contact with the adjacent teeth. The shells are designed with short interproximal and lingual side walls so that no trimming of the shells is needed. This, too, saves the dentist a great deal of time. The shells give the dentist several degrees of freedom, so that most molars and bicuspids can be fitted with only limited range of sizes and shapes of symmetric shells.

The present invention enables temporary or provisional crowns to be fitted to a patient quickly, half the time or less of the time required by prior techniques, to provide a good fit proximally, gingivally and occlusally, and to provide long term-durability.

The foregoing and other objects, features and advantages of the invention will become more readily apparent from the following detailed description of a preferred embodiment of the invention which proceeds with reference to the accompanying drawings.

DETAILED DESCRIPTION

Figure 1:
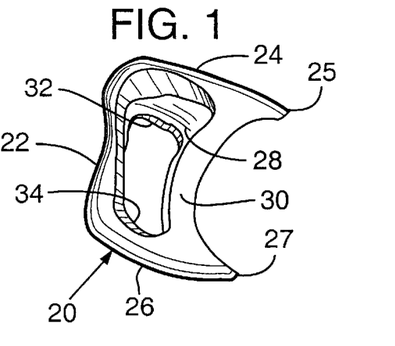
FIG. 1 is a side elevation view of a polycarbonate shell for making a temporary crown according to the first embodiment of the invention.

FIGS. 1–5 show the basic concept of the present invention in a first embodiment. FIG. 1 is a side elevation view of a shell 20 for making a temporary or long-term provisional bicuspid. This description likewise applies to a shell for a molar, which is described in further detail in connection with subsequent drawing figures. The shell 20 is preferably molded integrally of polycarbonate but can be made of other polymeric materials and can be made by machining. It has a top wall 22 defining an occlusal surface; a buccal sidewall 24; and a lingual sidewall 26 spaced from the buccal sidewall. The lingual sidewall 26 is shorter than the buccal sidewall 24, for ease of fitting the gingival margins 25, 27, as further discussed below. Opposite mesio-distal sidewalls 28, 30, are connected to the top wall and the buccal and lingual sidewalls and are spaced apart to define a central cavity to fit over a prepared tooth. The mesio-distal sidewalls are shorter occuluso-gingivally than the lingual and buccal sidewalls.

The mesio-distal sidewalls 28, 30 have windows 32, 34, each forming a partial opening in the respective sidewall for acrylic resin (see 36A, 38A in FIG. 2) to protrude from the cavity proximally to an adjacent tooth when the shell is fitted on a prepared tooth. The shell 20 can be made and used with a window in only one sidewall, but it is preferred to have such windows in both sidewalls. Each window has a size sufficient for resin to protrude proximally in amount sufficient to form a proximal contact to the adjacent tooth but sufficiently smaller than a surface area of the mesio-distal sidewall of the crown to control a flow of the resin from the cavity. The window shown in the embodiment of FIG. 1 has an area of about half the overall area of the mesio-distal sidewall of the shell.

Figure 2:
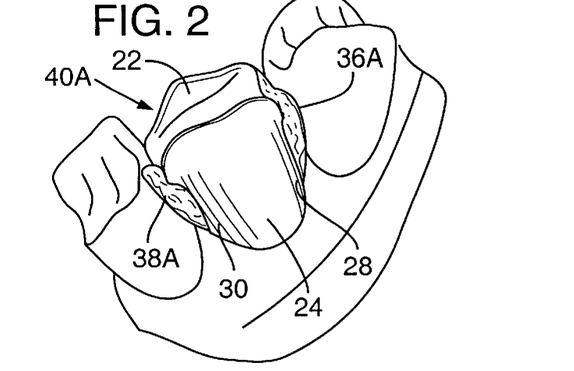
FIG. 2 is a perspective view of a temporary crown made with the shell of FIG. 1 and placed over a prepared tooth after being filled with Super T acrylic resin which extrudes through partial windows in the mesio-distal sides of the temporary crown.

FIGS. 2–5 show the present method of fabrication of temporary or long-term provisional crowns for molars and bicuspids using shells like shell 20. FIG. 2 is a perspective view of a portion of a patient's mouth showing a temporary crown 40A made with the polycarbonate shell 20 by filling the central cavity with a quantity of a Super T acrylic resin and positioning the shell and resin filler on the prepared tooth. Closing the patient's mouth clamps the resin filled shell 40A against an opposing tooth, thereby shaping the resin filler within the cavity to the prepared tooth. This step also establishes an occlusal contact of the occlusal surface of the shell with the opposing tooth, and extrudes a portion of the resin filler from the cavity through the windows in the mesio-distal sidewalls. The resin extruded through the windows when the patient bites down on the shell 20 forms extrusions 36A, 38A on the proximal sides of the temporary crown that contact the adjacent teeth. A portion of the mesio-distal sidewalls 28, 30 along the buccal and lingual margins of each window 32, 34 directs the extrusion of resin proximally toward the adjacent teeth.

Figure 3:
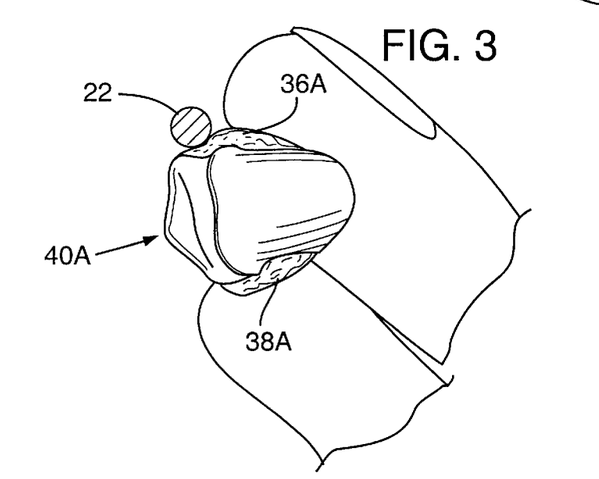
FIG. 3 is a perspective view of the temporary crown of FIG. 2 removed from the patient's tooth for shaping of the extruded resin using an acrylic burr.

FIG. 3 shows the temporary crown 40A of FIG. 2 removed from the patient's tooth and held in the dentist's fingers for shaping of the extruded resin using an acrylic burr 42 to contour its external surface to fit occlusally and proximally into the patient's dentition. This step includes trimming and shaping the acrylic resin extrusions 36A, 38A. Trimming of the gingival margins of shell 20 is generally unnecessary. The shells can be made in two lengths to fit a wide range of exposed tooth lengths. The shells are preferably formed with the lingual sidewall 26 sufficiently shorter than the buccal sidewall 24 to permit a degree of freedom in positioning the occlusal or top wall as the patient bites down without the gingival margin 27 of the lingual sidewall 26 engaging the patient's gingiva. This feature is explained further below.

Figure 4:
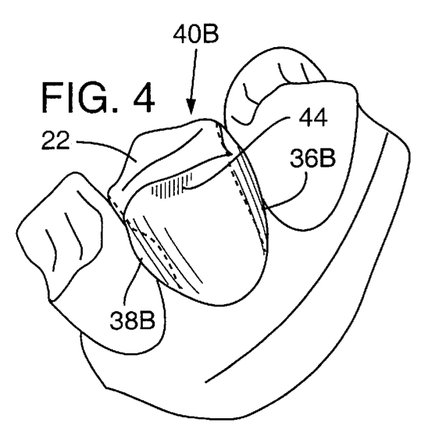
FIG. 4 is a perspective view similar to FIG. 2 showing the shaped temporary crown replaced on the patient's prepared tooth, shading along the edge the occlusal surface indicating an area to be ground for bite adjustment.
Figure 5:
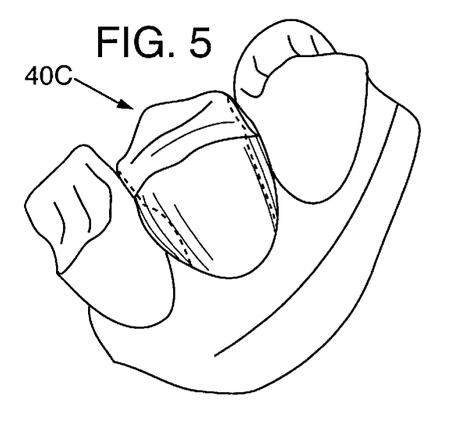
FIG. 5 is a view similar to FIG. 4 showing the temporary crown after shaping for bite adjustment, a broken line indicating the portion of the temporary crown formed by the extruded and shaped resin, which protrudes into the windows on the mesio side of the crown.

FIG. 4 shows the temporary crown 40B with shaped extrusions 36B, 38B, placed back on the patient's prepared tooth. Shading 44 along an edge of the occlusal surface 22 indicates a buccal cusp of the temporary crown to be ground for bite adjustment. FIG. 5 shows the temporary crown 40C after shaping for bite adjustment.

The entire procedure, from picking the proper size of shell for the prepared tooth (further described below) through filling, shaping and cementing the crown onto the prepared tooth, takes about half the time needed to complete temporary crowns using the prior art techniques, typically under 15 minutes.

A dashed line in FIGS. 4 and 5 indicates the portion of the temporary crown formed by the extruded and shaped resin, which protrudes through the partial windows on the proximal sides of the crown 40C. Once the crown is finished, the border between the shell and filler material is substantially smooth and nearly invisible except upon close inspection. The proximal fit to adjacent teeth will closely replicate that of a natural tooth, as will the occlusion with opposed teeth. The crown 40C will also be tightly sealed to the patient's tooth along the gingival margins. The resulting crown is composed of polycarbonate-reinforced acrylic resin which is very durable, suitable for use as a long-term provisional crown.

Figure 6:
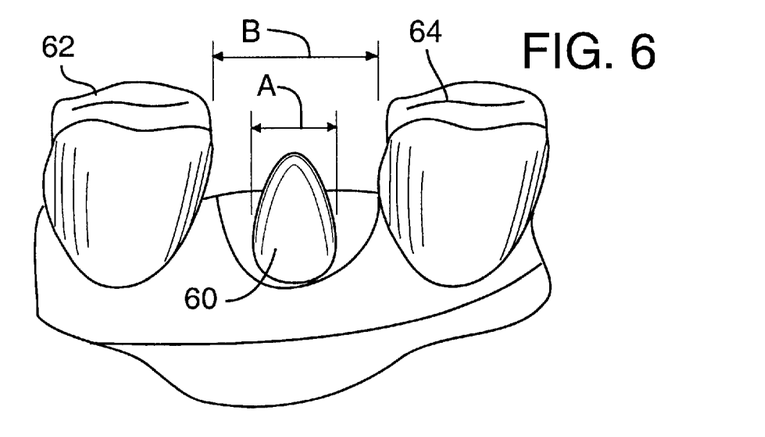
FIGS. 6 and 7 are side and plan views of a portion of a patient's dentition showing spacings used to select a shell of proper mesio-distal size to fit a prepared tooth according to the invention.
Figure 7:
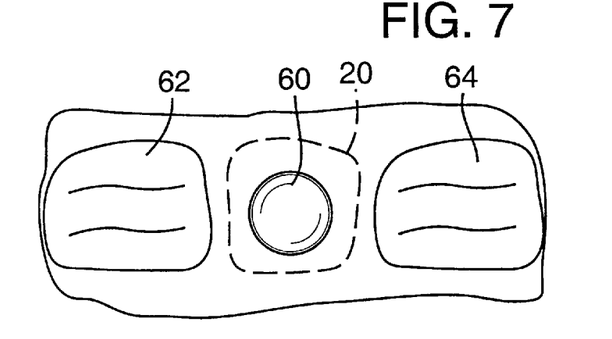
Figure 8:
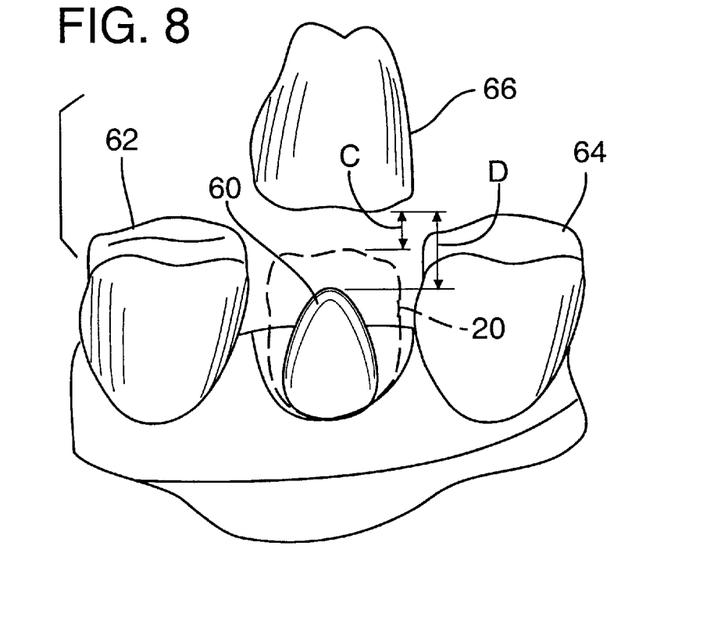
FIG. 8 is a side view similar to FIG. 6 showing sizing in the occluso-gingival direction.

FIGS. 6–8 show various views of a portion of a patient's dentition to illustrate the preferred spacings used to select a shell of proper mesio-distal and the occluso-gingival size to fit a prepared tooth 60 loosely between the adjacent teeth 62, 64 with the patient's bite in a closed position. FIGS. 6 and 7 show sizing of the shell 20 (shown in dashed lines in FIGS. 7 and 8) mesio-distally to position the mesio-distal sidewalls approximately halfway between mesio-distal surfaces of the teeth 62, 64 and those of the prepared tooth, i.e. midway between width A and width B in FIG. 6. The resulting position is shown by shell 20 in dashed lines in FIGS. 7 and 8. It is preferable to form a set of shells which includes shells for bicuspids and molars of at least two mesio-distal widths within the usual range of spacings for such teeth in permanent dentition. This sizing enables to dentist to select one of the shells for a given prepared tooth which has a mesio-distal width such that the shell passively fits between the adjacent teeth with a clearance in the range of half to one millimeter. The remaining proximal gap is filled by the resin filler protrusions 36A, 38A. This arrangement makes fitting the crown proximally very easy compared to prior art shells.

Referring to FIG. 8, the shell 20 is also sized to a length in an occluso-gingival direction to fit passively against an opposed tooth 66 with the patient's bite in a closed position over the unfilled shell. As mentioned above, a set of shells can include two different occluso-gingival lengths of a given bicuspid or molar, to accommodate the usual range of variations in tooth length that occurs among humans. For a given prepared tooth length, the shell is sized occluso-gingivally to provide a clearance C approximately half of the width D of the space between occlusal wall of the shell 20 and the opposed tooth 66. In selecting one of the shells to fit passively, the dentist will preferably choose the shell for a given tooth having an occluso-gingival length such that a gingival margin 25 of the shell approximately fits a gingival margin of the prepared tooth and the occlusal surface of the shell has a clearance from the opposed tooth 66 of half to one millimeter.

FIGS. 9–13 show various views of a second embodiment of a shell 120 for a bicuspid according to the invention. The general arrangement and procedure for making temporary and provisional crowns using shell 120 are largely the same as those described above for shell 120. Parts of shell 120 having corresponding parts in shell 20 are denoted by the same reference numerals, incremented by 100. Accordingly, shell 120 has an occlusal or top wall 122, buccal sidewalls 124, 126, with gingival margins 125, 127, respectively, and proximal sidewalls 128, 130.

The windows 132, 134 of shell 120 are U-shaped and are unbounded along the gingival margins of the proximal sidewalls, whereas the windows 32, 34 of shell 20 are bounded along the corresponding margins. Each of the windows 132, 134 is narrower than windows 32, 34 and preferably occupy an area that is about a third of the overall area of the proximal sidewall in which the window is formed.

Figures 9, 10, 11, 12:
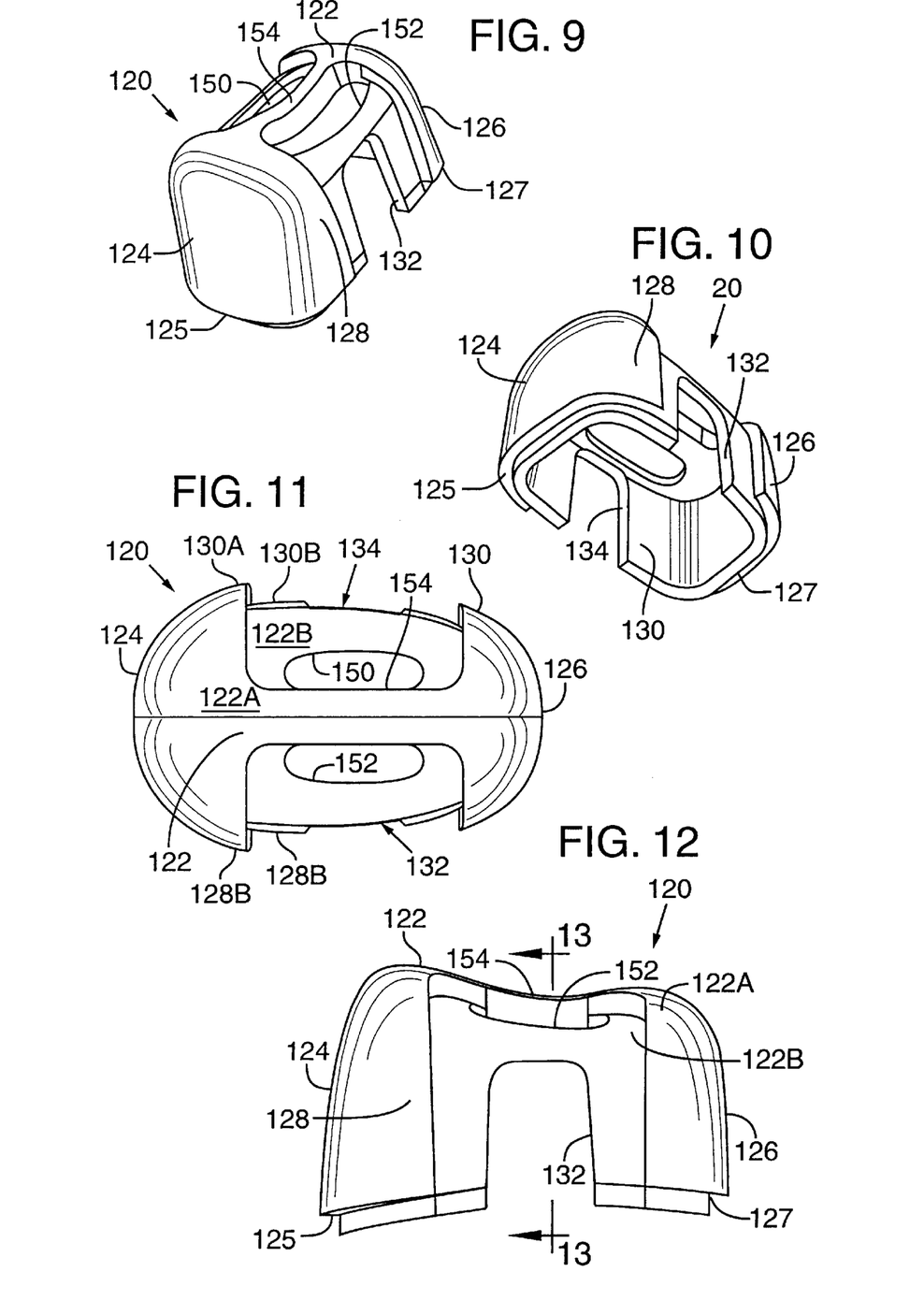
FIGS. 9 and 10 are top and bottom perspective views of a second embodiment of a shell for a bicuspid according to the invention.
FIGS. 11 and 12 are plan and side (mesio-distal) elevation views of the shell of FIGS. 9 and 10.

In the shell 120, the occlusal or top wall 122 also includes a window, preferably in this embodiment, a pair of windows 150, 152 in the form of elongate ovals spaced about a central bridge 154. The window or windows enable the extrusion of a portion of the filler resin from inside the central cavity of the shell onto the upper side of top wall 122 when the patient clamps down on the filled shell at the fabrication step shown in FIG. 2.

Figures 13, 14, 15, 16:
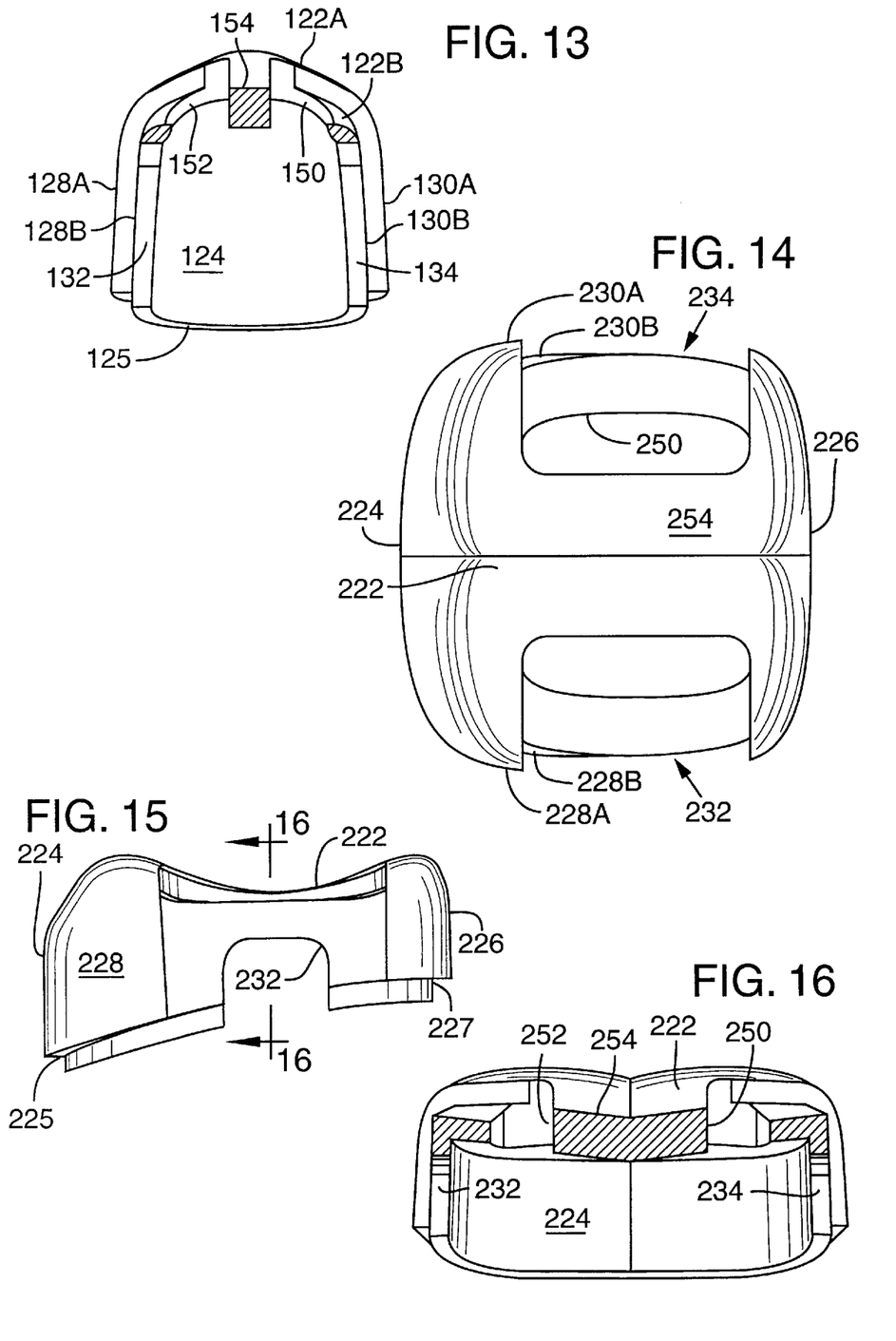
FIG. 13 is a cross-sectional view taken along lines 13—13 in FIG. 12.
FIGS. 14–16 are plan, side elevation and cross-sectional views similar to FIGS. 11–13 showing a shell for a molar according to the invention.

The top wall 122 of the shell 120 has an occlusal first surface 122A and further includes a recessed second surface 122B between the first surface and the window. The recessed surface forms a recessed margin around the window for receiving the resin filler extruded through windows 150, 152 and retaining the resin around the windows so as to be shaped by contact with the occlusal surface of an opposed tooth 66 (FIG. 8).

Similarly, the proximal surfaces of the shell 120 preferably include recessed areas 128B, 130B between the vertical sides of the windows 132, 134 and the shell's outermost proximal surfaces 128A, 130A. The recessed areas 128B, 130B form a recessed margin around the windows 132, 134 for receiving the resin filler extruded through such windows and retaining it in proximal contact to the adjacent teeth 62, 64 (FIG. 8).

In this embodiment, the gingival margins 125, 127 of the shell are also formed with a stair-step cross-sectional profile, which aids in receiving and retaining resin around the margins to form a superior seal with the prepared tooth. Another feature of this embodiment, is that the lingual sidewall 126 is shorter than the buccal sidewall by a ratio of about 3:4.

FIGS. 14–16 show a shell for a molar of essentially the same design as the second embodiment of bicuspid described above. Corresponding structural elements and features are indicated by the same reference numerals, incremented by 100, and need not be further described. The main difference from the bicuspid, aside from the difference in shape for use on molars, is that the lingual sidewall 226 is proportionately shorter than the buccal sidewall 224, this time by a ratio of about 2:3.

Figures 17, 18, 19, 20:
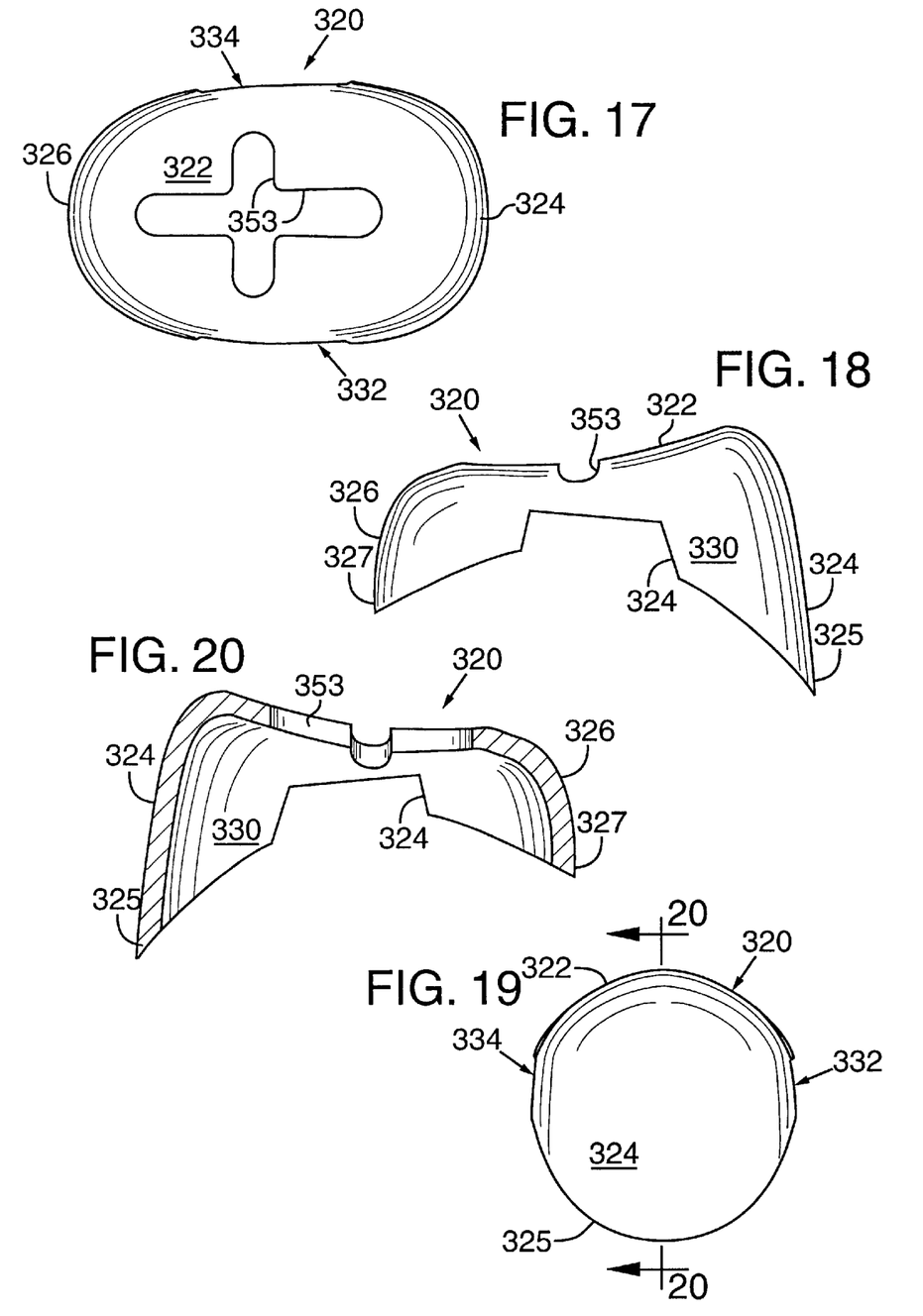
FIGS. 17–20 are plan, side elevation, buccal end and cross-sectional views of shell for a bicuspid according to a third embodiment of a the invention.
Figures 21, 22, 23, 24:
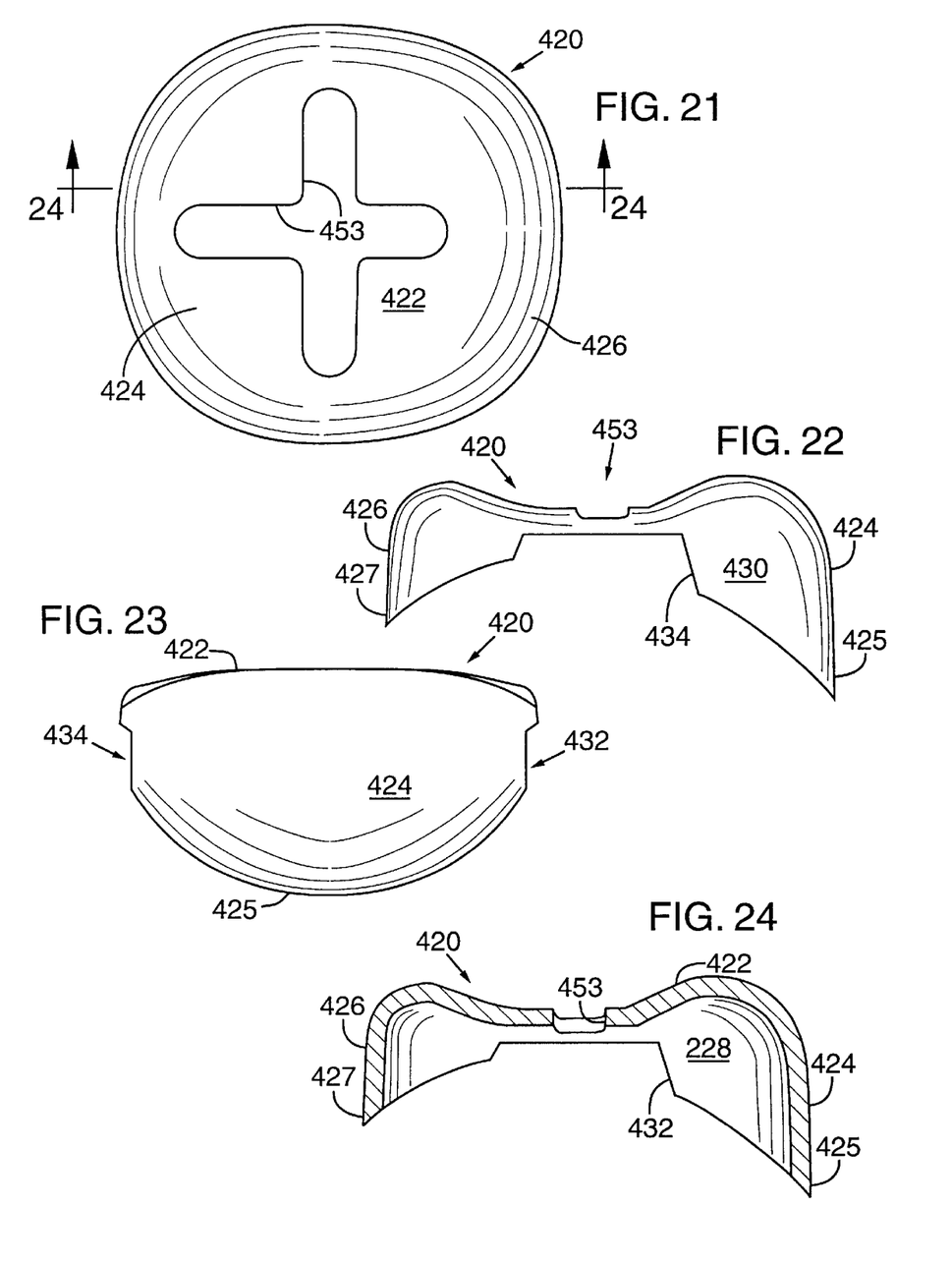
FIGS. 21–24 are plan, side elevation, buccal end and cross-sectional views of a shell for a molar according to the third embodiment of the invention.

FIGS. 17–24 show shells for a bicuspid 320 and a molar 420 according to a third embodiment of a the invention. Structural elements and features in common with the previously-described embodiments are indicated by like reference numerals incremented by 100. There are several differences in this embodiment. First, the top or occlusal sidewall 322, 422 has a single window 353, 453, which is cross-shaped, as best seen in FIGS. 17 and 21. This arrangement provides somewhat more area for extrusion of resin filler onto the top wall 322, 422 but still provides a narrow gap for supporting the filler in the finished crown. Second, the gingival margins of the shell are internally tapered, as shown by margins 325, 327 and 425, 427 in FIGS. 20 and 24, respectively.

A third difference is that the lingual sidewalls 326, 426 are proportionately shorter yet than the buccal sidewalls 324, 424, this time by a ratio of about 1:2. This ratio gives the greatest freedom of the gingival margin of the lingual sidewall to be positioned vertically along the lingual side of the prepared tooth so that the buccal cusp of the shell can move buccal-lingually about a gingival margin of the buccal sidewall. A shorter yet lingual sidewall could be used but without much further advantage in freedom of positioning the lingual margin or the buccal cusp, and with less control of flow of filler resin lingually when the patient bites down on the filled shell at the step shown in FIG. 2. The preferred material for this embodiment is a 20% fine fiber-glass filled polycarbonate. The resin is preferably Super-T glass-filled acrylic resin.

A further feature and advantage of the invention is best seen in the third embodiment. This embodiment incorporates a generic design suited to fit easily all four quadrants of a patient's dentition. A kit consisting of eight sizes and shapes of shells, four molars and four bicuspids, sized as shown in FIGS. 7 and 8, suffices to fit 95% of all permanent posterior dentition without trimming. The kit does not require right or left mirror-image shells for right or left dentition, nor does it require maxilla-specific and mandibular-specific shells. The shells 320, 420 are symmetrical about a buccal-lingual axis. All of the sidewalls of shells 320, 420 are short enough to fit passively (i.e., without interference with the prepared tooth, adjacent teeth and opposed teeth) when the patient's bite is in the closed position. The acrylic resin filler extrudes out of the mesio-distal sidewall in a controlled way to form good proximal contacts. The resin also extrudes along the gingival margins of the shell to form an accurate marginal seal on all sides of the prepared tooth. Because the lingual sidewall 326, 426 is substantially shorter than the buccal sidewall 324, 424, the shell 320, 420 is free to rotate about the facial gingival margin 325, 425 of the buccal sidewall as the patients bites down on the resin filled shell. This arrangement eliminates the need to trim the shell margins; facilitates properly positioning of the buccal cusp of the shell relative to opposed teeth; and reduces the need to trim excess resin and shell material from the faical (buccal) and occlusal surfaces of the crown.

Having described and illustrated the principles of the invention in a preferred embodiment thereof, it should be apparent that the invention can be modified in arrangement and detail without departing from such principles. Various novel features described herein can be used in different combinations and modified in shape and dimension. For example, a single oval window can be used in the occlusal surface; or the stairstep gingival margins of the second embodiment can be used in the first or third embodiment; or the recessed areas adjoining the windows in the second embodiment can be used in the other embodiments. I claim all modifications and variations coming within the spirit and scope of the following claims.

I claim:

1. A shell for making a temporary or long-term provisional crown comprising:
    a top wall defining an occlusal surface;
    a buccal sidewall;
    a lingual sidewall spaced from the buccal sidewall; and
    opposite mesio-distal sidewalls, connected to the top wall and buccal and lingual sidewalls and spaced apart to define a central cavity to fit over a prepared tooth;
    at least one of the mesio-distal sidewalls having a window forming a partial opening in the sidewall for resin to protrude from the cavity mesio-distally to an adjacent tooth, in which the mesio-distal sidewall includes a recessed area adjoining the window for receiving and retaining protruding resin in proximal contact with the adjacent tooth.

2. A shell according to claim 1 in which the window has a size sufficient for resin to protrude from the cavity mesio-distally in amount sufficient to form a proximal contact to the adjacent tooth but sufficiently smaller than a surface area of the mesio-distal sidewall of the crown to control a flow of the resin from the cavity.

3. A shell according to claim 1 in which the window has a size of approximately one-third to half of an area of the mesio-distal sidewall of the temporary crown.

4. A shell according to claim 1 in which the mesio-distal sidewall has a mesio-distal first surface and a recessed second surface between the first surface and the window, forming a recessed margin around the window for receiving and retaining protruding resin.

5. A shell according to claim 1 in which both mesio-distal sidewalls of the shell have one of said windows.

6. A shell according to claim 1 in which the top wall of the shell includes a window for resin to protrude occlusally from the cavity.

7. A shell according to claim 6 in which the top wall of the shell includes two of said windows spaced apart mesio-distally by a bridge extending in a buccal-lingual direction.

8. A shell according to claim 6 in which the top wall of the shell has an occlusal first surface and a recessed second surface between the first surface and the window, forming a recessed margin around the window to receive and retain resin around the window.

9. A shell according to claim 1 in which the buccal sidewall and the top wall form a buccal cusp, the buccal sidewall including the buccal cusp is sized in an occluso-gingival direction to a first length less than a length of a patient's tooth; and the lingual sidewall is sized in an occluso-gingival direction to a second length less than the first length of the buccal sidewall so that the buccal cusp of the shell is free to move buccal-lingually about a gingival margin of the buccal sidewall.

10. A shell according to claim 1 in which the window in the mesio-distal sidewall has a generally U-shape which is unbounded along a gingival periphery of the mesio-distal sidewall.

11. A set of shells according to claim 1 including two shells for molars and two shells for bicuspids, in which the mesio-distal sidewalls of the first and second shells for fitting a selected one of the molars and first and second shells for bicuspids include first and second widths, at least one of which can fit loosely on a prepared tooth between two adjacent teeth without trimming, so that the resin can protrude from the windows in the mesio-distal sidewalls to form a proximal contact to the adjacent teeth.

12. A shell for making a temporary or long-term provisional crown comprising:
    a top wall defining an occlusal surface;
    a buccal sidewall;
    a lingual sidewall spaced from the buccal sidewall; and
    opposite mesio-distal sidewalls, connected to the top wall and buccal and lingual sidewalls and spaced apart to define a central cavity to fit over a prepared tooth;
    the top wall and sidewalls being integrally formed of a polymeric material;
    each mesio-distal sidewall having a window forming a partial opening in the sidewall for resin to protrude from the cavity mesio-distally to an adjacent tooth; and
    each mesio-distal sidewall including a recessed area adjoining the window for receiving and retaining protruding resin securely in contact with the polymeric material.

13. A shell according to claim 12 in which the windows in the mesio-distal sidewalls have a generally U-shape which is unbounded along a gingival periphery of the mesio-distal sidewalls.

14. A shell according to claim 12 in which the mesio-distal sidewalls have a length shorter than a length of the buccal and lingual sidewalls.

15. A shell according to claim 12 in which the lingual sidewall has a length shorter than a length of the buccal sidewall.

16. A shell according to claim 12 in which each window has an area of about one-third of an area of the mesio-distal sidewall in which it is formed.

17. A shell for making a temporary or long-term provisional crown comprising:

a top wall defining an occlusal surface;
a buccal sidewall;
a lingual sidewall spaced from the buccal sidewall; and
opposite mesio-distal sidewalls, connected to the top wall and buccal and lingual sidewalls and spaced apart to define a central cavity to fit over a prepared tooth;
the buccal sidewall having a first length in a occluso-gingival direction and the lingual sidewall having a second length in the occluso-gingival direction which is less than the first length and each mesio-distal sidewall including a window forming a U-shaped partial opening in the sidewall for resin to protrude from the cavity proximally to the adjacent tooth and lingually to form a seal along a gingival margin of the shell.

18. A shell according to claim 17 in which the top wall and sidewalls are integrally formed of a polymeric material and the mesio-distal sidewalls include a recessed area adjoining the windows for receiving and retaining protruding resin securely in contact with the polymeric material.

19. A shell according to claim 17 in which the buccal sidewall and the top wall form a buccal cusp, the buccal sidewall including the buccal cusp is sized in an occluso-gingival direction to a first length less than a length of a patient's tooth; and the lingual sidewall is sized in an occluso-gingival direction to a second length less than the first length of the buccal sidewall so that the buccal cusp of the shell is free to move buccal-lingually about a gingival margin of the buccal sidewall.

20. A shell according to claim 17 in which the mesio-distal sidewalls include recessed areas adjoining the windows for receiving and retaining protruding resin in proximal contact with the adjacent teeth.

21. A shell according to claim 17 in which the top wall includes a window forming a partial opening for resin to protrude occlusally from the cavity to an opposed tooth.

22. A shell according to claim 21 in which the top wall includes a recessed areas adjoining the window for receiving and retaining protruding resin in position to be shaped by contact with the opposed tooth.

23. A shell according to claim 17 in which the sidewalls include recessed areas along a gingival periphery thereof for receiving and retaining protruding resin in sealing contact along a gingival margin of a prepared tooth.

24. A shell according to claim 17 in which the buccal sidewall includes a detachable tab for handling the shell during making of the crown.

25. A set of shells according to claim 17 including multiple shells sized and shaped to fit permanent human bicuspids and molars, each of the shells shaped symmetrically about a buccal-lingual axis so that a shell of a selected size can fit interchangeably a tooth on the patient's right or left side and a mandibular or maxillary tooth.

26. A set of shells according to claim 25 including at least one shell for a molar and one shell for a bicuspid, in which each of the shells is sized to mesio-distally to position the mesio-distal sidewalls approximately halfway between a mesio-distal side of a prepared tooth and a mesio-distal side of an adjacent tooth.

27. A shell according to claim 17 in which the mesio-distal sidewalls have a length shorter than a length of the buccal and lingual sidewalls.

28. A shell according to claim 17 in which each window has an area of about one-third of an area of the mesio-distal sidewall in which it is formed.

29. A method for fabrication of temporary or long-term provisional crowns for molars and bicuspids, the method comprising:
forming a shell comprising a top wall defining an occlusal surface, opposite buccal and lingual sidewalls, and opposite mesio-distal sidewalls spaced apart to define a central cavity to fit over a prepared tooth in a patient's mouth, with a window forming a partial opening in each mesio-distal sidewall;
forming the mesio-distal sidewalls with a recessed area adjoining the windows for receiving and retaining protruding resin in proximal contact with adjacent teeth;
filling the central cavity with a quantity of a resin filler;
positioning the shell and resin filler on the prepared tooth;
closing the patient's mouth to clamp the prepared tooth and resin filled shell against an opposing tooth, thereby shaping the resin filler within the cavity to the prepared tooth, establishing an occlusal contact of the occlusal surface of the shell with the opposing tooth, and extruding a portion of the resin filler from the cavity through the windows in the mesio-distal sidewalls to form a proximal contact to adjacent teeth;
removing the shell with shaped and extruded resin filler from the prepared tooth; and
shaping the shell and extruded resin filler to contour an external surface thereof to fit occlusally and proximally into the patient's dentition.

30. A method according to claim 29 in which the forming step includes sizing the shell to fit loosely between the adjacent teeth with the patient's bite in a closed position.

31. A method according to claim 30 in which the shell is sized mesio-distally to position the mesio-distal sidewalls approximately half of the distance between the prepared tooth and mesio-distal surfaces of the teeth adjacent the prepared tooth.

32. A method according to claim 30 in which the forming step includes forming a set of shells including shells of at least two mesio-distal widths and selecting one of the shells having a mesio-distal width such that the shell passively fits between the adjacent teeth with a clearance in the range of half to one millimeter.

33. A method according to claim 29 in which the shell is sized to a length in an occluso-gingival direction to fit passively against an opposed tooth with the patient's bite in a closed position.

34. A method according to claim 33 in which the shell is sized occluso-gingivally to position the top wall approximately half way between the prepared tooth and the opposed tooth.

35. A method according to claim 33 in which the forming step includes forming a set of shells including shells of at least two occluso-gingival lengths and selecting one of the shells having an occluso-gingival length such that a gingival margin of the shell approximately fits a gingival margin of the prepared tooth and the occlusal surface of the shell has a clearance from the opposed tooth of half to one millimeter.

36. A method according to claim 29 in which the buccal sidewall of the shell includes a buccal cusp and is sized in an occluso-gingival direction to a first length less than a length of a patient's tooth and the lingual sidewall is sized in to a second length less than the first length so that the buccal cusp is free to move buccal-lingually about a gingival margin of the buccal sidewall when the resin filled shell is clamped onto the prepared tooth.

37. A method according to claim 29 in which the step of closing the patient's mouth extrudes a portion of the resin from the shell along a gingival margin of at least the lingual sidewall of the shell to form a sealing contact to the prepared tooth.

38. A method according to claim 29 in which the forming step includes forming a set of shells, the set including first and second shells for fitting a selected one of the molars and bicuspids in which the buccal sidewalls have first lengths and the lingual sidewalls have second lengths, less than the respective first lengths, to fit teeth of different lengths without trimming.

39. A method according to claim 29 in which the shell is formed so that the windows in the mesio-distal sidewalls have a generally U-shape which is unbounded along a gingival periphery of the mesio-distal sidewalls.

40. A method according to claim 29 in which the shell is formed so that the mesio-distal sidewalls have a length shorter than a length of the buccal and lingual sidewalls.

41. A method according to claim 29 in which the shell sidewalls are sized to a length relative to the prepared tooth so that a portion of the resin protrudes to form a seal along a gingival margin of the shell.

* * * * *

UNITED STATES PATENT AND TRADEMARK OFFICE
CERTIFICATE OF CORRECTION

PATENT NO.   : 6,068,481
DATED        : May 30, 2000
INVENTOR(S)  : Worthington

It is certified that error appears in the above-identified patent and that said Letters Patent is hereby corrected as shown below:

Column 2,
Line 43, "temporary crown" should read -- temporary or long-term provisional crown --
Lines 56-57, "long term-durability" should read -- long-term durability --

Column 3,
Line 60, "occuluso-gingivally" should read -- occluso-gingivally --

Column 5,
Line 15, "enables to dentist" should read -- enables the dentist --

Column 6,
Line 33, "of a the invention" should read -- of the invention --

Signed and Sealed this

Second Day of April, 2002

Attest:

*Attesting Officer*

JAMES E. ROGAN
*Director of the United States Patent and Trademark Office*